United States Patent [19]

Yamamoto et al.

[11] Patent Number: 5,559,231

[45] Date of Patent: * Sep. 24, 1996

[54] SPIRO-OXAZINE COMPOUNDS

[75] Inventors: Shinichi Yamamoto, Kyoto; Takashi Taniguchi, Shiga, both of Japan

[73] Assignee: Toray Industries, Inc., Tokyo, Japan

[*] Notice: The portion of the term of this patent subsequent to Dec. 20, 2012, has been disclaimed.

[21] Appl. No.: 283,945

[22] Filed: Aug. 1, 1994

Related U.S. Application Data

[63] Continuation of Ser. No. 38,073, Mar. 29, 1993, Pat. No. 5,374,723, which is a continuation of Ser. No. 425,205, filed as PCT/JP89/00124 Feb. 8, 1989, abandoned.

[30] Foreign Application Priority Data

Feb. 8, 1988 [JP] Japan .................................. 63-27327
May 27, 1988 [JP] Japan ................................. 63-130833

[51] Int. Cl.$^6$ .............................................. C07D 491/10
[52] U.S. Cl. ................................................. 544/70; 544/71
[58] Field of Search ............................... 544/71, 70

[56] References Cited

U.S. PATENT DOCUMENTS

| | | | |
|---|---|---|---|
| 4,634,767 | 1/1987 | Hoelscher et al. | 544/71 |
| 5,000,878 | 3/1991 | Chu | 544/71 |
| 5,017,698 | 5/1991 | Machida et al. | 544/71 |
| 5,166,345 | 11/1992 | Akashi et al. | 544/71 |

FOREIGN PATENT DOCUMENTS

| | | |
|---|---|---|
| 62-205185 | 3/1986 | Japan . |
| 63-30488 | 2/1988 | Japan . |
| 8907104 | 8/1989 | WIPO . |

OTHER PUBLICATIONS

Glenn H. Brown, Photochromism, vol. III, Techniques of Chemistry, pp. 45–99, Wiley Interscience, New York, 1971.

*Primary Examiner*—Nicholas Rizzo

*Attorney, Agent, or Firm*—Birch, Stewart, Kolasch & Birch, LLP

[57] ABSTRACT

A spiro-oxazine compound represented by the following general formula (A) or (A') is a photochromic compound having an excellent fatigue resistance to repetition of coloration and decoloration and an abundance of hues:

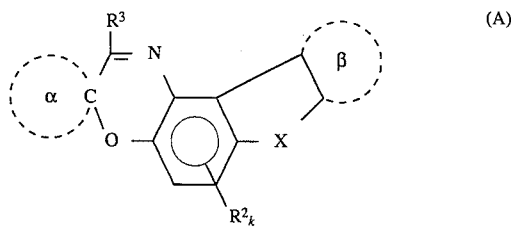

(A)

or

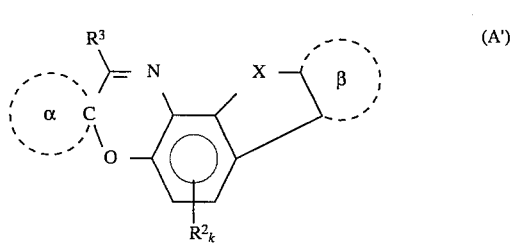

(A')

wherein the α ring is a ring selected from a 5-membered ring having one N atom, which may be connected to a benzene ring or naphthalene ring, and a 6-membered ring having one N atom, with the proviso that the N atom in the e ring is bonded to a $C_{1-20}$ alkyl or another organic group, X is selected from O, S, Se and N–$R^1$ (in which $R^1$ is selected from H, and $C_{1-20}$ alkyl and other organic groups), $R^2$ and $R^3$ are selected from —OH, amino, $C_{1-20}$ alkoxy, halogen, and other groups, and k is an integer of 0 to 2.

2 Claims, No Drawings

SPIRO-OXAZINE COMPOUNDS

This application is a continuation of application Ser. No. 08/038,073, filed on Mar. 29, 1993, now 5,384,723, which was a continuation application of Ser. No. 07/425,205, filed on Oct. 6, 1989, now abandoned, the entire contents of which are hereby incorporated by reference.

TECHNICAL FIELD

The present invention relates to a spiro-oxazine compound. More particularly, the present invention relates to a photochromic compound valuable as a printing material, an optical recording material, a recording material, a clothing material, a decorating material and the like.

BACKGROUND ART

A spiropyran compound can be mentioned as a typical photochromic compound, and many photochromic spiropyran compounds are known [G. H. Brown, "Photochromism", Wiley Interscience, New York (1971)].

Spiropyran compounds, however, have a problem of poor fatigue resistance at the repetition of coloration and decoloration.

A spiro-oxazine compound is known as a photochromic compound having an improved fatigue resistance. For example, Japanese Unexamined Patent Publication No. 62-205185 discloses the following compound:

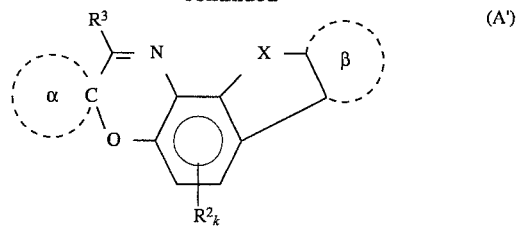

However, In the conventional spiro-oxazine compounds, however, the hue of the chromophoric seed is limited to violet-to-blue, and thus they have a low selection of hues.

DISCLOSURE OF THE INVENTION

The present invention is intended to overcome the above-mentioned defects of the conventional technique, and an object of the present invention is to provide a photochromic compound having an excellent fatigue resistance upon a repetition of coloration and decoloration and an abundance of hues. According to the present invention, the above-mentioned object,is obtained by providing a spiro-oxazine compound represented by the following general formula (A) or (A'):

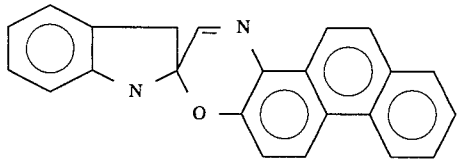

or

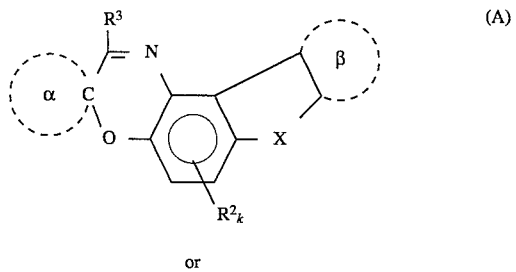

wherein the α ring is a ring selected from the group consisting of a 5-membered ring having one nitrogen atom, a 5-membered ring having one nitrogen atom and connected to a benzene ring or naphthalene ring and a 6-membered ring having one nitrogen atom, with the proviso that the nitrogen atom in the α ring is bonded to an organic group $R^0$ as expressed as >N–$R^0$ (in which $R^0$ stands for a substituent selected from the group consisting of an alkyl group having 1 to 20 carbon atoms, an alkenyl group having 2 to 20 carbon atoms, an aralkyl group having 7 to 20 carbon atoms and an aryl group having 6 to 19 carbon atoms); the β ring is a benzene ring or a naphthalene ring, X stands for one member selected from the group consisting of O, S, Se and N–$R^1$ (in which $R^1$ stands for one member selected from the group consisting of a hydrogen atom, an alkyl group having 1 to 20 carbon atoms, an alkenyl group having 2 to 20 carbon atoms, an aralkyl group having 7 to 20 carbon atoms, an aryl group having 6 to 19 carbon atoms and an acyl group having 2 to 20 carbon atoms); $R^2$ and $R^3$ stand for a substituent selected from the group consisting of a hydroxyl group, an amino group, an alkoxy group having 1 to 20 carbon atoms, an aralkoxy group having 7 to 15 carbon atoms, an aryloxy group having 6 to 14 carbon atoms, an acyloxy group having 2 to 20 carbon atoms, an alkyl group having 1 to 20 carbon atoms, an alkenyl group having 2 to 20 carbon atoms, an aralkyl group having 7 to 15 carbon atoms, an aryl group having 6 to 14 carbon atoms, a halogen group, a cyano group, a carboxyl group, a nitro group (not included in $R^3$), an acyl group having 2 to 20 carbon atoms, an alkoxycarbonyl group having 2 to 20 carbon atoms, a carbamoyl group, a carbamoyloxy group and a sulfonic acid group (not included in $R^3$), with the proviso that a hydrogen atom is included in $R^3$; and k is an integer of from 0 to 2.

BEST MODE FOR CARRYING OUT THE INVENTION

In the compound of the present invention represented by the general formula (A) or (A'), the α ring is a 5-membered or 6-membered ring having one nitrogen atom, or a 5-membered ring having one nitrogen atom and connected to a benzene ring or naphthalene ring. As specific examples, there can be mentioned a pyrrolidine ring, a pyrrole ring, a piperidine ring, a tetrahydropyridine ring, a dihydropyridine ring, an indoline ring, and a benzindoline ring.

The nitrogen atom contained in the α ring is bonded to an organic group $R^0$ as expressed as >N–$R^0$.

As specific examples of the substituent $R^0$, there can be mentioned linear alkyl groups having 1 to 20 carbon atoms, such as methyl, ethyl and octadecyl groups, branched alkyl groups having 3 to 20 carbon atoms, such as tert-butyl and 2-methylpentyl groups, cycloalkyl groups having 3 to 10 carbon atoms, such as cyclohexyl, norbornyl and adamantyl groups, alkenyl groups having 2 to 20 carbon atoms, such as vinyl, allyl, hexenyl, 1,3-butadienyl and isopropenyl groups, aralkyl groups having 7 to 20 carbon atoms, such as benzyl, phenethyl and (2-naphthyl)methyl groups, and aryl groups having 6 to 19 carbon atoms, such as phenyl and 2-naphthyl groups. $R^0$ may be substituted. As specific examples of the substituent for $R^0$, there can be mentioned a hydroxyl group, amino groups such as amino, dibenzylamino and (2-methacryloxyethyl)amino groups, alkoxy groups such as methoxy, ethoxy and propoxy groups, acyloxy groups such as acetoxy, benzoyloxy, acryloxy and methacryloxy groups, alkyl groups such as methyl, ethyl, trifluoromethyl and butyl groups, aralkyl groups such as benzyl and 4-(2,3-epoxypropyl)phenethyl groups, aryl groups such as phenyl and styryl groups, halogen groups such as fluoro and chloro groups, a cyano group, a carboxyl group, a nitro group, an acetyl group, acyl groups such as acetyl and mythlacryl groups, alkoxycarbonyl groups such as ethoxycarbonyl and 3,4-epoxybutyloxycarbonyl groups, carbamoyl groups such as carbamoyl, N-phenylcarbamoyl and N-(2-methacryloxy)-ethylcarbamoyl groups, carbamoyloxy groups such as an [N-(acryloxy)propylcarbamoyl]oxy group, and sulfonic acid groups such as a sulfonic acid group and metal salts thereof (for example, sodium and lithium salts).

The β ring, which is included in the general formula (A) or (A') as well as the α ring, is a benzene ring or a naphthalene ring.

Other constituents included in the general formula (A) or (A') will now be described.

X is one member selected from the group consisting of O, S, Se and N–$R^1$ in which $R^1$ stands for one member selected from the group consisting of a hydrogen atom, an alkyl group having 1 to 20 carbon atoms, an alkenyl group having 2 to 20 carbon atoms, an aralkyl group having 7 to 20 carbon atoms, an aryl group having 6 to 19 carbon atoms and an acyl group having 2 to 20 carbon atoms. $R^1$ may be substituted. As specific examples of the alkyl, alkenyl, aralkyl and aryl groups as $R^1$, inclusive of substituents contained in $R^1$, there can be mentioned those exemplified above with respect to $R^0$, and as the acyl group, there can be mentioned an acetyl group and a methacryl group.

In order to obtain a compound having an excellent repetition durability and having a plurality of absorption bands of the chromophoric seed, X is preferably O. Furthermore, to obtain a chromophoric seed of a bright red hue, X is preferably N–$R^1$.

As specific examples of $R^2$ and $R^3$, there can be mentioned a hydroxyl group, substituted and unsubstituted amino groups such as amino, dimethylamino, dibenzylamino and (2-methacryloxyethyl)amino groups, alkoxy groups having 1 to 20 carbon atoms, such as methoxy, ethoxy, propoxy and butoxy groups, aralkoxy groups having 7 to 15 carbon atoms, such as benzyloxy and phenethyloxy groups, aryloxy groups having 6 to 14 carbon atoms, such as phenoxy and naphthyloxy groups, acyloxy groups having 2 to 20 carbon atoms, such as benzoyloxy, acryloxy and methacryloxy groups, alkyl groups having 1 to 20 carbon atoms, such as methyl, ethyl, propyl, butyl, tert-butyl, glycidyl and octadecyl groups, alkenyl groups having 2 to 20 carbon atoms, such as vinyl, allyl, isopropenyl, 1,3-butadienyl and 9,12-octadecadienyl groups, aralkyl groups having 7 to 15 carbon atoms, such as benzyl, phenetyl and naphthylmethyl groups, aryl groups having 6 to 14 carbon atoms, such as phenyl and naphthyl groups, halogen groups such as chloro, fluoro and bromo groups, a cyano group, a carboxyl group, a nitro group (not included in $R^3$), acyl groups having 2 to 20 carbon atoms, such as acetyl, methacryl and acryl groups, alkoxycarbonyl groups having 2 to 20 carbon atoms, such as ethoxycarbonyl and 3,4-epoxybutyloxycarbonyl groups, unsubstituted and substituted carbamoyl groups such as carbamoyl, N-phenylcarbamoyl and N-(2-methacryloxy)ethylcarbamoyl groups, carbamoyloxy groups such as [N-(3-acryloxy)propylcarbamoyl]oxy and [N-(methacryloxy)propylcarbamoyl]oxy) groups, and sulfonic acid groups (not included in $R^3$) such as a sulfonic acid group and metal salts thereof (for example, sodium and lithium salts). Furthermore, a hydrogen atom is included in $R^3$.

Note, k is an integer of from 0 to 2, and where k is 2, two $R^2$ groups may be the same or different.

As specific examples of the spiro-oxazine compound of the present invention represented by the general formula (A) or (A'), there can be mentioned the following compounds.

(a) Spiro-oxazine compounds represented by the following general formula (B) or (B'):

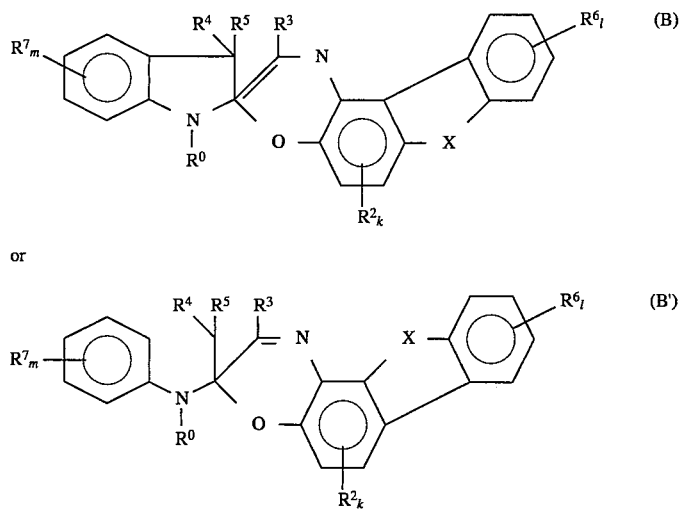

wherein $R^0$, $R^2$, $R^3$, X and k are as defined in the general formula (A) or (A'), $R^4$ and $R^5$ independently stand for a substituent selected from the group consisting of an alkyl group having 1 to 20 carbon atoms, an aralkyl group having 7 to 20 carbon atoms and an aryl group having 6 to 19 carbon atoms, or $R^4$ and $R^5$ together form a cycloalkyl group having 3 to 10 carbon atoms with the carbon atom at the 3-position, $R^6$ and $R^7$ stand for a substituent selected from the group consisting of a hydroxyl group, an amino group, an alkoxy group having 1 to 20 carbon atoms, an aralkoxy group having 7 to 15 carbon atoms, an aryloxy group having 6 to 14 carbon atoms, an acyloxy group having 2 to 20 carbon atoms, an alkyl group having 1 to 20 carbon atoms, an alkenyl group having 2 to 20 carbon atoms, an aralkyl group having 7 to 15 carbon atoms, an aryl group having 6 to 14 carbon atoms, a halogen group, a cyano group, a carboxyl group, a nitro group, an acyl group having 2 to 20 carbon atoms, an alkoxycarbonyl group having 2 to 20 carbon atoms, a carbamoyl group, a carbamoyloxy group and a sulfonic acid group, and l and m stand for an integer of from 0 to 4.

(b) Spiro-oxazine compounds represented by the following general formula (C) or (C'):

atoms, an alkenyl group having 2 to 20 carbon atoms, an aralkyl group having 7 to 15 carbon atoms, an aryl group having 6 to 14 carbon atoms, a halogen atom, a cyano group, a carboxyl group, a nitro group, an acyl group having 2 to 20 carbon atoms, an alkoxycarbonyl group having 2 to 20 carbon atoms, a carbamoyl group, a carbamoyloxy group and a sulfonic acid group, and n is an integer of from 0 to 2.

(c) Spiro-oxazine compounds represented by the following general formula (D) or (D'):

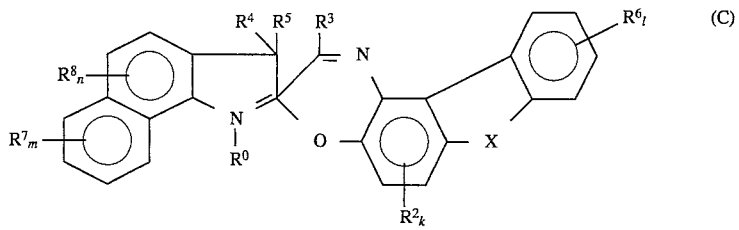

(C)

or

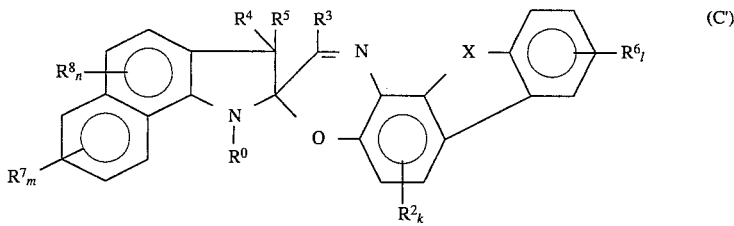

(C')

wherein $R^0$, $R^2$, $R^3$, X and k are as defined in the general formula (A) or (A'), $R^4$, $R^5$, $R^6$, $R^7$, l and m are as defined in the general formula (B) or (B'), $R^8$ stands for a substituent selected from the group consisting of a hydroxyl group, an

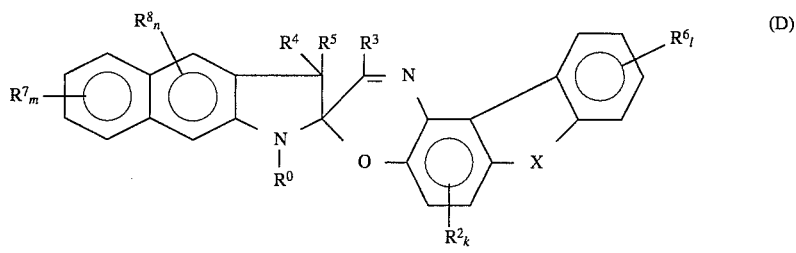

(D)

or

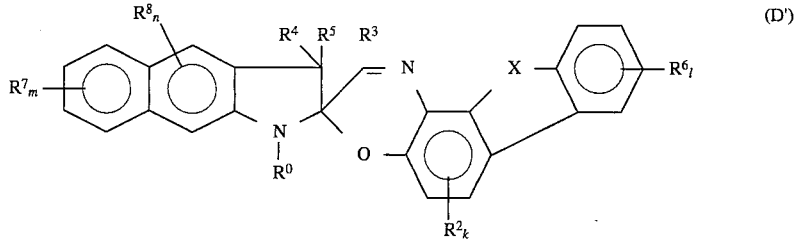

(D')

amino group, an alkoxy group having 1 to 20 carbon atoms, an aralkoxy group having 7 to 15 carbon atoms, an aryloxy group having 6 to 14 carbon atoms, an acyloxy group having 2 to 20 carbon atoms, an alkyl group having 1 to 20 carbon wherein $R^0$, $R^2$, $R^3$, X and k are as defined in the general formula (A) or (A'), $R^4$, $R^5$, $R^6$, $R^7$, l and m are as defined in the general formula (B) or (B'), and $R^8$ and n are as defined in the general formula (C) or (C').

(d) Spiro-oxazine compounds represented by the following general formula (E) or (E'):

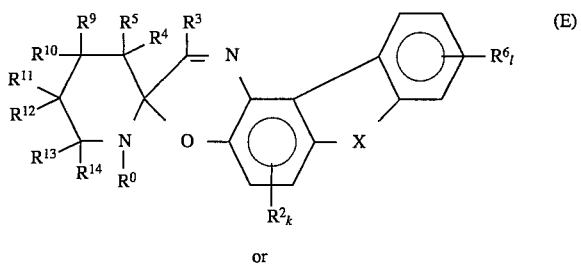

or

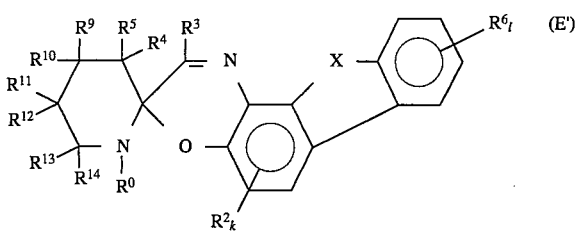

wherein $R^0$, $R^2$, $R^3$, X and k are as defined in the general formula (A) or (A'), $R^4$, $R^5$, $R^6$ and l are as defined in the general formula (B) or (B'), and $R^9$, $R^{10}$, $R^{11}$, $R^{12}$, $R^{13}$ and $R^{14}$ stand for one member selected from the group consisting of a hydrogen atom, an alkyl group having 1 to 20 carbon atoms, an aralkyl group having 7 to 20 carbon atoms, and an aryl group having 6 to 19 carbon atoms.

(e) Spiro-oxazine compounds represented by the general formula (F) or (F'):

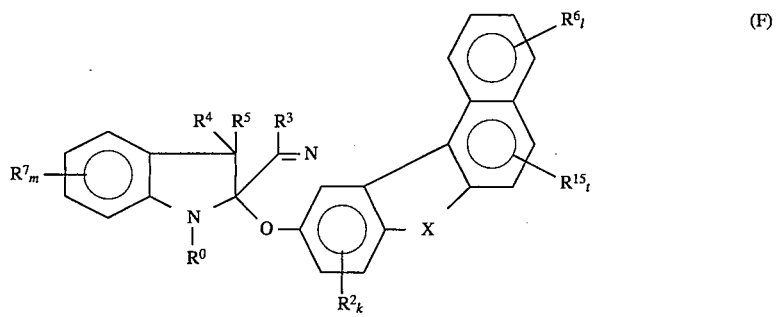

or

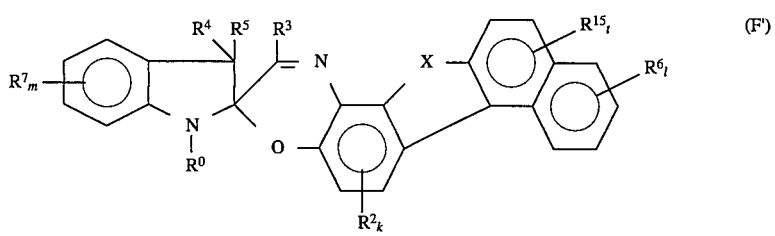

wherein $R^0$, $R^2$, $R^3$, X and k are as defined in the general formula (A) or (A'), $R^4$, $R^5$, $R^6$ and $R^7$, l and m are as defined in the general formula (B) or (B'), $R^{15}$ stands for a substituent selected from the group consisting of a hydroxyl group, an amino group, an alkoxy group having 1 to 20 carbon atoms, an aralkoxy group having 7 to 15 carbon atoms, an aryloxy group having 6 to 14 carbon atoms, an acyloxy group having 2 to 20 carbon atoms, an alkyl group having 1 to 20 carbon atoms, an alkenyl group having 2 to 20 carbon atoms, an aralkyl group having 7 to 15 carbon atoms, an aryl group having 6 to 14 carbon atoms, a halogen atom, a cyano group, a carboxyl group, a nitro group, an alkoxycarbonyl group having 2 to 20 carbon atoms, a carbamoyl group, a carbamoyloxy group and a sulfonic acid group, and t is an integer of from 0 to 2.

In the spiro-oxazine compounds represented by the above-mentioned general formulae (B), (B'), (C), (C'), (D) and (D') as specific examples of $R^4$ $R^5$ which are independent from each other, there can be mentioned linear alkyl groups having 1 to 20 carbon atoms, such as methyl, ethyl and octadecyl groups, branched alkyl groups having 3 to 20 carbon atoms, such as a 2-methylpentyl group, cycloalkyl groups having 3 to 10 carbon atoms, such as a cyclohexyl group, aralkyl groups having 7 to 20 carbon atoms, such as benzyl and phenethyl groups and aryl groups having 6 to 19 carbon atoms, such as a phenyl group, and as specific examples of the group formed by combined $R^4$ and $R^5$ together with the carbon at the 3-position, there can be mentioned cycloalkyl groups having 3 to 10 carbon atoms, such as cyclohexyl, norbornyl and adamantyl groups.

$R^4$ and $R^5$ may be substituted. As the substituent for $R^4$ and $R^5$ there can be mentioned those exemplified above as the substituent for $R^0$.

$R^6$, $R^7$ and $R^8$ are as defined in the general formula (A) or (A') with respect to $R^2$. l, m and n are as defined above, and if they are 2 or more, two or more of corresponding $R^6$, $R^7$ or $R^8$ groups may be the same or different.

In the spiro-oxazine compounds represented by the above-mentioned general formula (E) or (E'), $R^0$, $R^2$, $R^3$, $R^4$, $R^5$, $R^6$, X, k and l are as defined in the above-mentioned general formulae (A), (A'), (B), (B'), (C), (C'), (D) and (D') and $R^9$, $R^{10}$, $R^{11}$, $R^{12}$, $R^{13}$ and $R^{14}$ are selected from the group consisting of a hydrogen atom and the same alkyl, aralkyl and aryl groups as exemplified above with respect to $R^2$ in the general formula (A) or (A'). All of these groups may be the same or different.

In the spiro-oxazine compounds represented by the general formula (F) or (F'), groups other than $R^{15}$ are as mentioned in the other general formulae, and $R^{15}$ is selected from groups exemplified above with respect to $R^0$ in the general formula (A) or (A'). If t is 2, two $R^{15}$ groups may be the same or different.

As is apparent from the foregoing description, the spiro-oxazine compound of the present invention is characterized in that the spiro-oxazine compound comprises not only the above-mentioned α ring but also an oxazine ring, a benzene ring, a heterocyclic 5-membered ring and the β ring. Especially, a compound in which the benzene ring, heterocyclic 5-membered ring and β ring are consecutively by connected, $R^3$ is a hydrogen atom and X is O, S or Se, has absorption peaks in both of the short wavelength region (less than 550 nm) and long wavelength region (more than 600 nm) of the visible ray region, and even a compound developing a green color can be obtained. Furthermore, if $R^3$ has a substituent other than hydrogen or X is $N–R^1$, a compound developing a red color can be obtained. Accordingly, the spiro-oxazine compound of the present invention has an abundance of chromophoric seed. Moreover, the spiro-oxazine compound of the present invention has an excellent fatigue resistance to the repetition of coloration and decoloration.

The general formulae (A) and (A') in the present invention are isomeric to each other, and an appropriate isomer is selected according to the intended object in view of the kinds of substituents and the desired photochromic characteristics.

The compound of the present invention represented by the formula (A) or (A') is prepared, for example, according to the following processes.

According to the first process, a methylene compound represented by the following general formula (I):

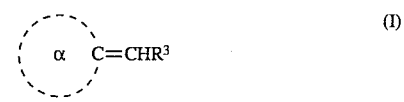

is reacted with a nitroso compound represented by the following general formula (II) or (II'):

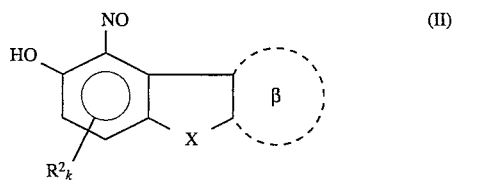

to prepare a compound represented by the formula (A) or (A').

According to the second process, a compound represented by the following general formula (III):

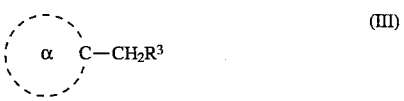

is reacted with a quaternarizing agent $R^0$—Y (Y stands for an anionic leaving group), a basic substance and a compound represented by the general formula (II) or (II') in an optional order to obtain a compound represented by the formula (A) or (A').

According to the third process, a reaction product between a compound represented by the formula (I) and nitrous acid is reacted with an amino compound represented by the following general formula (IV) or (IV'):

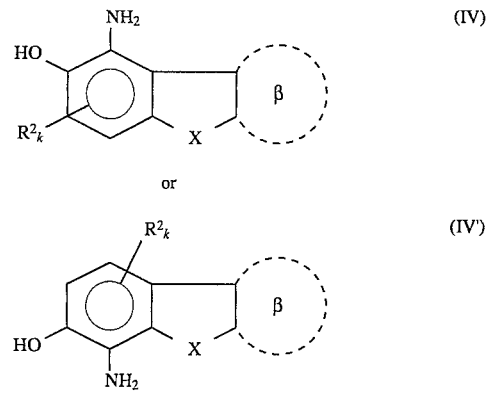

to prepare a compound represented by the formula (A) or (A').

According to the fourth process, a reaction product between a compound represented by the formula (III) and nitrous acid is reacted with a quaternarizing agent $R^0$—Y, a basic substance and a compound represented by the general formula (IV) or (IV'), in an optional order to prepare a compound represented by the formula (A) or (A').

According to the fifth process, a reaction product between a compound represented by the following general formula (V):

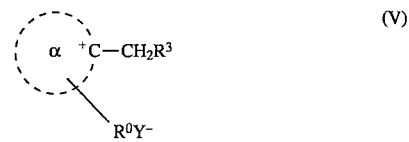

and nitrous acid is reacted with a basic substance and a compound represented by the general formula (IV) or (IV') in an optional order to prepare a compound represented by the formula (A) or (A').

As the purification method in the preparation process, preferably recrystallization using various solvents, column chromatography separation using a silica column or the like, solvent extraction and active carbon treatment are adopted.

The spiro-oxazine compound of the present invention is preferably used in combination with an optically transparent resin. As the resin, there can be mentioned, for example, a diethylene glycol bis-allylcarbonate polymer, a (meth-)acrylic polymer, a copolymer thereof, a cellulose, polyvinyl acetate, polyvinyl alcohol, polyvinyl butyral, a polyester resin, polycarbonate, polystyrene, a copolymer thereof, an epoxy resin, a (hatogenated) bisphenol A di(meth)acrylate polymer, a copolymer thereof, a (halogenated) bisphenol A urethane-modified di(meth)acrylate polymer, a copolymer thereof, a nylon resin and polyurethane.

If-the spiro-oxazine compound of the present invention has an alkenyl group, that is, a polymerizable functional group such as a methacryloxy group or a vinyl group, by copolymerization of this spiro-oxazine compound with other polymerizable compound such as an acrylic monomer, a styrene type monomer or a vinyl acetate type monomer, the spiro-oxazine compound can be integrated with a polymer resin of the other polymerizable compound. If the spiro-oxazine compound is thus integrated by the copolymerization, a preferred photochromic material having an excellent durability of the spiro-oxazine compound can be obtained.

Compounds of the general formulae (A) through (F) and (A') through (F') having polymerizable functional groups at $R^0$, $R^2$, $R^6$, $R^7$ and $R^{15}$ are preferable from the viewpoint of the durability. Compounds having a polymerizable functional group at $R^0$ which is introduced through a methylene chain having at least 3 carbon atoms, are especially preferred. A methacryloxy group is especially preferred as the polymerizable functional group, because the radical polymerization is easily accomplished and decomposition is prevented during the polymerization.

If the compound of the present invention has a polymerizable functional group, the compound can be used in the form of not only a copolymer as mentioned above but also a homopolymer.

The photochromic compound of the present invention can be preferably used as an optical element having photochromic characteristics in the form of a combination with a resin, a polymer of the compound or a combination of this polymer with other resin. As the optical element, there can be mentioned sunglass lens, ski goggles and protective glass lens. Furthermore, the photochromic compound of the present invention can be preferably used for curraining, clothing, automobile windows such as a front glass or sun roof, toys, toilet articles and writing tools.

As the method for combining the photochromic compound of the present invention, various methods can be adopted, for example, a dyeing method, a casting method and a polymer solution-coating method. Instead of the polymer solution-coating method, a method can be adopted in which an emulsion is formed and the emulsion is coated by screen printing. Moreover, various printing methods, for example, a gravure printing method, can be adopted. As the coating method, various coating methods can be adopted, such as a dip coating method, a spin coating method and a roll coating method.

In many cases, the chromophoric seed of the compound of the present invention has at least two absorption peaks, and therefore, the compound of the present invention is valuable as a material for a rewritable optical disk.

The amount of the compound of the present invention to be combined with the resin should be determined according to the object and the application method, but from the viewpoint of visual sensitivity, preferably the amount of the compound of the present invention is 0.01 to 20% by weight based on the resin.

To improve the repetition durability of the photochromic compound of the present invention, preferably oxygen and water are intercepted when the compound of the present invention is used. Furthermore, known additives can be used to further improve the durability. For example, there can be used a single oxygen quencher represented by a nickel salt, an antioxidant represented by a hindered amine or a polymer thereof and an ultraviolet absorber having no influence on the photochromic characteristics.

The present invention will now be described in detail with reference to the following examples that by no means limit the scope of the invention.

EXAMPLE 1

(1) Synthesis of 1-Nitroso-2-Hydroxydibenzofuran

In 100 g of pyridine was dissolved 10 g of 2-hydroxydibenzofuran, and the solution was cooled to 0° C. Then, 60 g of a 20% aqueous solution of sodium nitrite was added to the above solution and 100 g of a 30% aqueous solution of sulfuric acid was added dropwise to the mixture while stirring for 10 minutes. After the dropwise addition, the mixture was stirred at 0° C. for 1 hour and then filtered. The recovered solid was washed with water and dried to obtain 11 g of a red crystal of 1-nitroso-2-hydroxydibenzofuran.

(2) Results of Analysis

| | Elementary analysis values: | |
|---|---|---|
| | Found Value (%) | Calculated Value (%) |
| C | 67.7 | 67.7 |
| H | 3.2 | 3.3 |
| N | 6.3 | 6.6 |

NMR (protons other than OH): 6.7 ppm (d, 1H), 7.4 ppm (t, 1H), 7.5 ppm (t, 1H), 7.6 ppm (d, 1H), 7.7 ppm (d, 1H), 8.3 ppm (d, 1H)

(3) Synthesis of Spiro-oxazine of Following Formula (G):

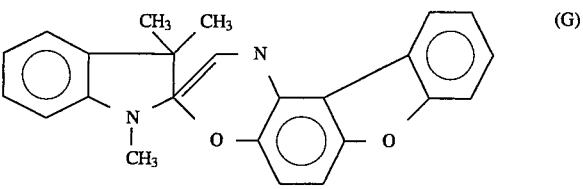

In 100 ml of absolute ethanol were dissolved 10 g of 1,3,3-trimethyl-2-methylene-indoline and 10 g of 1-nitroso-2-hydroxydibenzofuran, and reaction was carried out at the reflux temperature for 1 hour. After the reaction, the reaction mixture was concentrated and subjected to column chromatography separation using silica gel as the supporting carrier and methylene chloride as the developing solvent. Distillation of methylene chloride gave a pink solid, and recrystallization from methanol gave a white crystal of the spiro-oxazine of the formula (G).

(4) Results of Analysis

| | Elementary analysis values: | |
|---|---|---|
| | Found Value (%) | Calculated Value (%) |
| C | 78.8 | 78.3 |
| H | 5.8 | 5.4 |
| N | 7.2 | 7.6 |

NMR: 1.4 ppm (6H), 2.8 ppm (3H), 6.6–8.5 ppm (11H)

Melting point: 158° C.

(5) Application

A coating solution was prepared by dissolving 0.1 g of the spiro-oxazine of the formula (G) in 100 g of a 10% solution of polyvinyl butyral in butanol, and the coating solution was coated on two glass sheets. The coated glass sheets were dried and piled so that the resin-coated surfaces confronted each other, and the piled glass sheets were heated.

When the so-prepared photochromic laminated glass was irradiated with ultraviolet rays, the laminated glass became green. If the light was removed and the laminated glass was allowed to stand in the dark, the laminated glass became colorless again. When the laminated glass was irradiated with light for 20 hours in a fade meter and the light resistance was examined, it was found that the photochromic characteristics were the same as those before the placement in the fade meter, and it was confirmed that the fatigue resistance was excellent. When the absorption characteristics at the time of coloration in methanol were examined, it was found that absorption peaks $\lambda_{max}$ appeared at 460 nm and 632 nm.

EXAMPLE 2

(1) Synthesis of spiro-oxazine of following formula (S):

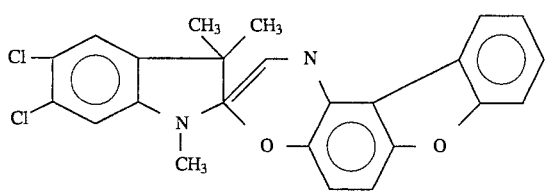

A white crystal of the spiro-oxazine of the formula (S) was obtained in the same manner as described in Example 1 except that 1,3,3-trimethyl-2-methylene-5,6-dichloroindoline was used instead of 1,3,3-tri-methyl-2-methyleneindoline.

(2) Results of Analysis

| Elementary analysis values: | | |
|---|---|---|
| | Found Value (%) | Calculated Value (%) |
| C | 66.1 | 65.9 |
| H | 3.8 | 4.1 |
| N | 6.5 | 6.4 |

Melting point: 204°–205° C.
NMR: 1.5 ppm (6H), 2.8 ppm (3H), 6.4–8.4 ppm (9)H (3) Application A laminated glass was prepared in the same manner as described in Example 1 by using the so-obtained compound. When the laminated glass was irradiated with ultraviolet rays, the laminated glass became green, and if the light was removed and the laminated glass was allowed to stand in the dark, the laminated glass became colorless again. When the laminated glass was irradiated with light for 20 hours in a fade meter and the light resistance was examined, it was found that the photochromic characteristics were the same as those before the placement in the fade meter and the light resistance was excellent.

EXAMPLE 3

(1) Synthesis of Spiro-oxazine of Formula (H)

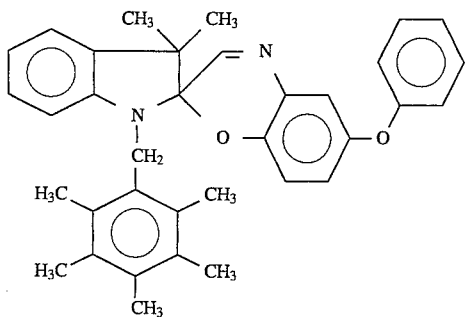

In 100 ml benzene were dissolved 10 g of 2,3,3,-trimethylindolenine and 15 g of 2,3,4,5,6-pentamethylbenzyl chloride, and the solution was refluxed for 2 hours. Then, the temperature of the reaction liquid was lowered to about 50° C., and 3 g of triethylamine and 10 g of 1-nitroso-2-hydroxydibenzofuran were added to the reaction liquid. Reaction was carried out at the reflux temperature for 1 hour. Then, the purification was carried out in the same manner as described in Example 1 to obtain a white crystal of the spiro-oxazine of the formula (G).

(2) Results of Analysis

| Elementary analysis values: | | |
|---|---|---|
| | Found Value (%) | Calculated Value (%) |
| C | 81.9 | 81.7 |
| H | 6.8 | 6.6 |
| N | 5.2 | 5.4 |

NMR: 1.4 ppm (6H), 2.2 ppm (15H), 4.3 ppm (2H), 6.4–8.5 ppm (11H)

(3) Application

A laminated glass was prepared in the same manner as described in Example 1 by using the so-prepared compound. When the absorption characteristics of the laminated glass at the time of coloration were examined, it was found that the absorption peaks $\lambda_{max}$ appeared at 460 nm and 632 nm.

EXAMPLES 4 THROUGH 11

(1) The following compounds having substituents at the positions a through g were prepared in the same manner as described in Example 3.

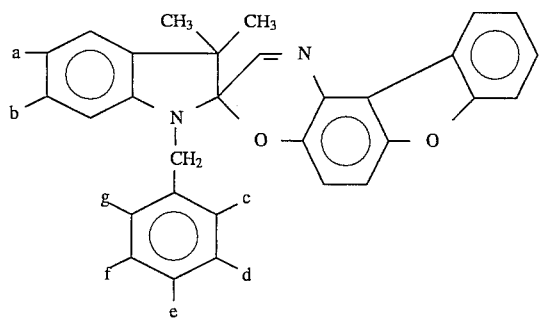

The compound of Example 4 had Cl at each of the positions a, b, c and e.

The compound of Example 5 had F at each of the positions c, d, e, f and g.

The compound of Example 6 had $OCH_3$ at each of the positions a and c and $NO_2$ at the position e.

The compound of Example 7 had a methacryloxy group at the position a.

The compound of Example 8 had a methoxy group at the position a and a vinyl group at the position e.

The compound of Example 9 had H at each of the positions a through g.

The compound of Example 10 had Cl at each of the positions c and e.

The compound of Example 11 had $CH_3$ at the position d.

(2) Results of Analysis

| | Elementary analysis values: | | |
|---|---|---|---|
| | C (%) | H (%) | N (%) |
| Example 4 | 62.2 | 3.5 | 4.7 |
| | (61.9) | (3.4) | (4.8) |
| Example 5 | 67.5 | 3.9 | 5.0 |
| | (67.4) | (3.6) | (5.2) |
| Example 6 | 70.3 | 5.2 | 7.6 |
| | (69.9) | (4.9) | (7.7) |
| Example 7 | 77.1 | 5.2 | 5.3 |
| | (77.3) | (5.3) | (5.3) |
| Example 8 | 79.0 | 5.3 | 5.7 |
| | (79.2) | (5.6) | (5.6) |

-continued

|  | Elementary analysis values: | | |
|---|---|---|---|
|  | C (%) | H (%) | N (%) |
| Example 9 | 81.1 | 5.3 | 6.3 |
|  | (81.1) | (5.4) | (6.3) |
| Example 10 | 70.2 | 4.0 | 5.5 |
|  | (70.2) | (4.3) | (5.5) |
| Example 11 | 81.0 | 5.8 | 6.0 |
|  | (81.2) | (5.7) | (6.1) |

Each value is a found value but each of the parenthesized values is a calculated value.

NMR:

Example 9: 1.4 ppm (6H), 4.4 ppm (4H), 6.3–8.4 ppm (16H)

Example 10: 1.4 ppm (6H), 4.5 ppm (2H), 6.3–8.4 ppm (14H)

Example 11: 1.4 ppm (6H), 2.3 ppm (3H), 4.5 ppm (2H), 6.2–8.5 ppm

Melting point:

Example 9: 157°–158° C.

Example 10: 150° C.

(3) Application

Laminated glasses were prepared in the same manner as described in Example 1 by using the compounds of Examples 4 through 6. Each of the laminated glasses became green under irradiation with ultraviolet rays.

In 20 g of toluene were dissolved 1 g of the compound of Example 7 and 10 g of n-butyl methacrylate, and solution polymerization was carried out by using azobisisobutyronitrile as the polymerization initiator. When the polymer solution was coated on a slide glass, a transparent coating film was obtained. When the glass sheet was irradiated with ultraviolet rays, the glass sheet became green, and when the light was removed and the glass sheet was allowed to stand in the dark, the glass sheet became colorless again.

A glass sheet was similarly prepared by using the compound of Example 8, and the glass sheet became green under irradiation with ultraviolet rays.

A coating solution formed by dissolving 0.1 g of the compound of Example 9 in a 10% solution of an acrylic polymer in toluene was coated on two glass sheets. The glass sheets were dried and piled so that the resin-coated surfaces confronted each other, and the laminate then heated.

When the so-prepared photochromic laminated glass was irradiated with ultraviolet rays, the laminated glass became green, and when the light was removed and the laminated glass was allowed to stand in the dark, the laminated glass became colorless again. When the laminated glass was irradiated with light for 20 hours in a fade meter and the light resistance was examined, it was found that the photochromic characteristics were the same as those before the placement in the fade meter and the light resistance was excellent. When the absorption characteristics an the time of coloration were examined, it was found that the absorption peaks $\lambda_{max}$ appeared at 486 nm and 632 nm.

A laminated glass was prepared in the same manner as described above by using the compound of Example 10, and when the absorption characteristics at the time of coloration were examined, it was found that the absorption peaks $\lambda_{max}$ appeared at 486 nm and 628 nm.

A coating solution comprising 0.1 g of the compound of Example 11, 0.03 g of a hindered amine type light stabilizer (LA-57 supplied by Adeca-Argus), 0.04 g of a hindered amine type light stabilizer (LA-77 supplied by Adeca-Argus), 0.02 g of a hindered phenol type antioxidant (AO-60 supplied by Adeca-Argus), 0.01 g of di(2-ethylhexyl) adipate as a plasticizer, 0.1 g of dimethyl diphenate and 100 g of a 10% solution of polyvinyl butyral in butanol was coated on two glass sheets. The coated glass sheets were dried and piled so that the resin-coated surfaces confronted each other, and the laminate then heated. When the so-prepared photochromic laminated glass was irradiated with ultraviolet rays, the laminated glass became green, and when the light was removed and the laminated glass was allowed to stand in the dark, the laminated glass became colorless again. When the laminated glass was irradiated with light for 20 hours in a fade meter and the light resistance was examined, it was found that the light resistance was good.

EXAMPLE 12

(1) Synthesis of spiro-oxazine of following formula (I):

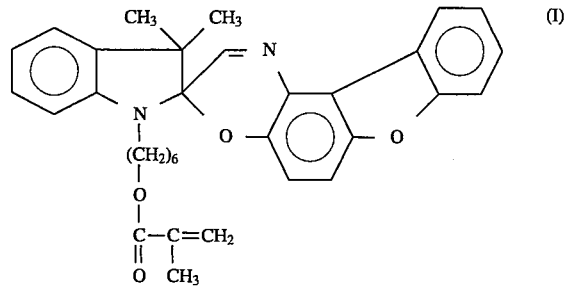

To a solution comprising 15 g of 1-(6-hydroxyhexyl)-2,3,3-trimethylindolenium iodide, 10 g of triethylamine and 100 ml of methylene chloride was added dropwise 15 g of methacryloyl chloride. After the dropwise addition, the mixture was stirred for 1 hour. Then, 100 ml of water was added to the mixture, and the mixture was extracted with methylene chloride. The methylene chloride layer was concentrated to obtain 11 g of 1-(6-methacryloxy)hexyl-2-methylene-3,3-dimethylindoline. The reaction was carried out in the same manner as described in Example 1 except that the so-obtained compound was used instead of 1,3,3-trimethyl-2-methylene-indoline, whereby a yellow liquid of the spiro-oxazine of the formula (I) was obtained.

(2) Results of Analysis

|  | Elementary analysis values: | |
|---|---|---|
|  | Found Value (%) | Calculated Value (%) |
| C | 75.8 | 75.9 |
| H | 6.4 | 6.5 |
| N | 5.4 | 5.4 |

IR: 1720 cm$^{-1}$

NMR: 1.2–2.0 ppm (17H), 3.2 ppm (2H), 4.1 ppm (2H), 5.5 ppm (1H), 6.1 ppm (1H), 6.6–8.5 ppm (11H)

(3) Application

In the same manner as described in Example 7, a coated glass sheet was prepared by using the spiro-oxazine of the formula (I). When the glass sheet was irradiated with ultraviolet rays, the glass sheet became green, and when the light was removed and the glass sheet was allowed to stand in the dark, the glass sheet became colorless again. When the absorption characteristics at the time of coloration were examined, it was found that the absorption peaks $\lambda_{max}$ appeared at 486 run and 633 nm.

When the glass sheet was subjected to the durability test where the glass sheet was irradiated with light for 20 hours in a fade meter, no substantial degradation was observed, and it was confirmed that the glass sheet had a good durability.

EXAMPLE 13

(1) Synthesis of spiro-oxazine compound of formula (J)

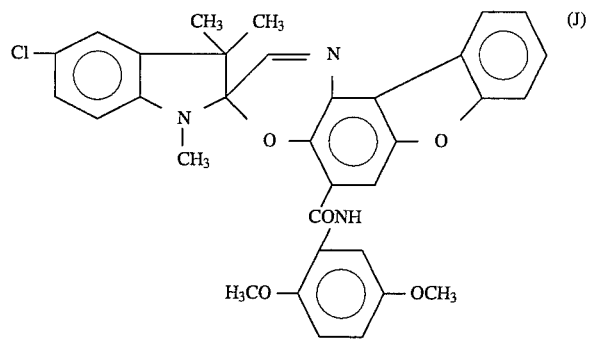

The above compound was synthesized in a manner similar to the manner adopted in Example 1.

(2) Results of Analysis

| Elementary analysis values: | |
|---|---|
| Found Value (%) | Calculated Value (%) |
| C 72.2 | 72.4 |
| H 5.4 | 5.3 |
| N 7.4 | 7.7 |

IR: 3380 cm$^{-1}$, 3340 cm$^{-1}$, 1710 cm$^{-1}$,
1540 cm$^{-1}$, 1250 cm$^{-1}$, 1025 cm$^{-1}$ (3) Application The spiro-oxazine of the formula (J) was dissolved in methyl methacrylate at a concentration of 0.5% by weight, and cast polymerization was carried out by using azobisisobutyronitrile as the polymerization initiator to obtain a polymethyl methacrylate sheet in which the compound of the formula (J) was incorporated.

When the sheet was irradiated with ultraviolet rays, the sheet became green, and when the light was removed and the sheet was allowed to stand in the dark, the sheet promptly became colorless again. When the absorption characteristics at the time of coloration were examined, it was found that the absorption peaks $\lambda_{max}$ appeared at 490 nm and 706 nm. This sheet became green even at 50° C. under irradiation with ultraviolet rays, and the coloration-possible temperature was higher than 50° C.

EXAMPLE 14

(1) Synthesis of 2,3,3-trimethylbenz(g)indolenine

To 10 g of 1-naphthylhydrazine hydrochloride and 30 g of methyl isopropyl ketone was added dropwise 5 g of sulfuric acid, and reaction was carried out at the reflux temperature for 2 hours. The reaction mixture was neutralized with a 20% aqueous solution of sodium hydroxide and extracted with water/ether, and the ether layer was concentrated to obtain 8 g of 2,3,3-trimethylbenz(g)indolenine.

(2) Synthesis of 1,2,3,3-tetramethylbenz(g)-indolenium iodide

A solution comprising 8 g of 2,3,3-trimethylbenz(g)indolenine and 25 g of methyl iodide was reacted at the reflux temperature for 30 minutes. The formed precipitate was recovered by filtration and washed with acetone to obtain 12 g of a white crystal.

(3) Synthesis of spiro-oxazine of following formula (K):

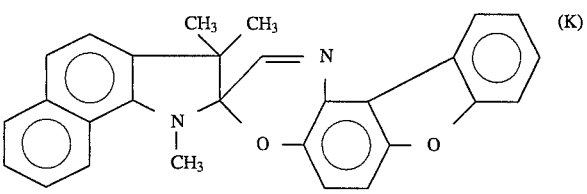

A solution of 12 g of 1,2,3,3-tetramethylbenz(g)indolenium iodide and 10 g of 1-nitroso-2-hydroxydibenzofuran in 50 ml of isopropanol was heated to 50° C., and 5 g of piperidine was added to the solution. Then, reaction was carried out at the reflux temperature for 1 hour. The reaction mixture was concentrated and subjected to the column chromatography separation using silica gel as the supporting carrier and toluene as the developing solvent. Distillation of the solvent gave a pink solid. When this solid was recrystallized from butanol, a light yellow crystal of the compound of the formula (K) was obtained.

(4) Results of Analysis

| Elementary analysis values: | |
|---|---|
| Found Value (%) | Calculated Value (%) |
| C 80.5 | 80.4 |
| H 5.6 | 5.3 |
| N 6.4 | 6.7 |

NMR: 1.4 ppm (6H), 3.4 ppm (3H), 6.4–8.7 ppm (13H)

(5) Application

A laminated glass was prepared in the same manner as described in Example 9 by using the compound of the formula (K). When the laminated glass was irradiated with ultraviolet rays, the laminated glass became green, and when the light was removed and the laminated glass was allowed to stand in the dark, the laminated glass became colorless again. When the laminated glass was irradiated with light for 20 hours in a fade meter and the light resistance was examined, it was found that the photochromic characteristics were the same as those before the placement in the fade meter and the fatigue resistance was excellent. When the absorption characteristics at the-time of coloration were examined, it was found that the absorption peaks $\lambda_{max}$ appeared at 465 nm and 650 nm.

EXAMPLES 15 THROUGH 18

Compounds of the following formula having substituents at the positions a and b were synthesized in a manner similar to the manner adopted in Example 7:

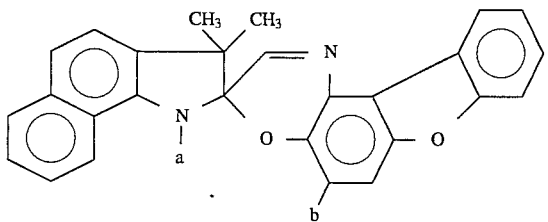

The compound of Example 15 had $$-CH_2-\underset{a}{\underset{|}{\bigcirc}}-CH_3$$

at the position a.

The compound of Example 16 had —CH$_3$ at the position a and —CO$_2$H at the position b.

The compound of Example 17 had —CH$_3$ at the position a and —CH$_2$OH at the position b.

The compound of Example 18 had $$-CH_2CH\underset{O}{-}CH_2$$

at the position a and $$-CH_2OC\overset{O}{\underset{\|}{-}}C(CH_3)=CH_2$$

at the position b.

(2) Results of Analysis

| | Elementary analysis values: | | |
|---|---|---|---|
| | C (%) | H (%) | N (%) |
| Example 15 | 82.9 | 5.3 | 5.4 |
| | (82.7) | (5.5) | (5.5) |
| Example 16 | 75.3 | 4.7 | 6.0 |
| | (75.3) | (4.8) | (6.1) |
| Example 17 | 77.4 | 5.3 | 6.2 |
| | (77.7) | (5.4) | (6.3) |
| Example 18 | 75.2 | 5.2 | 4.7 |
| | (75.3) | (5.4) | (5.0) |

Each value is a found value, but each of the parenthesized values is a calculated value.

Laminated glasses were prepared in the same manner as described in Example 9 by using the compounds of Examples 15 through 17. Each of the laminated glasses became green under irradiation with ultraviolet rays.

A glass sheet was prepared in the same manner as described in Example 7 by using the compound of Example 18. The glass sheet became green under irradiation with ultraviolet rays.

EXAMPLE 19

(1) Synthesis of 2,3,3-trimethylbenz(f)indolenine

Reaction was carried out in the same manner as described in (1) of Example 14 except that 2-naphthylhydrazine hydrochloride was used instead of 1-naphthylhydrazine hydrochloride (2) Synthesis of Spiro-oxazine of Following Formula (L):

(L)

[Structural formula of spiro-oxazine compound with CH$_3$, CH$_3$, N, CH$_3$, O, and Br substituents]

In 40 ml of ethanol were dissolved 6 g of the compound prepared in (1) above and 10 g of methyl rosylate, and reaction was carried out at the reflux temperature for 2 hours. The temperature of the reaction liquid was lowered to 50° C., and 2 g of triethylamine and 10 g of 1-nitroso-2-hydroxy-8bromodibenzofuran were added to the reaction liquid. Reaction was carried out at the reflux temperature for 2 hours, and the subsequent procedures were the same as described in Example 1 and a light yellow crystal of the compound of the formula (L) was obtained.

(3) Results of Analysis

| | Elementary analysis values: | |
|---|---|---|
| | Found Value (%) | Calculated Value (%) |
| C | 67.3 | 67.6 |
| H | 4.0 | 4.2 |
| N | 5.7 | 5.6 |

EXAMPLE 20

(1) Synthesis of 4,4-Dimethyl-5-Oxohexane-Nitrile

A mixture of 40 g of 3-methyl-2-butanone and 2 g of Triton B was heated to 35° C., and 20 g of acrylonitrile was added to the mixture over a period of 1 hour. Then, the mixture was stirred for 18 hours, and hydrochloric acid was added to the mixture to make the mixture acidic and the mixture was extracted with ether.

(2) Synthesis of Compound of Following Formula (VI):

$$CH_3-\underset{\underset{\displaystyle\overset{O}{\underset{CH_2}{\diagup}}\overset{\displaystyle C-CH_3}{\underset{CH_2}{\diagdown O}}}{\overset{\displaystyle CH_3}{\displaystyle |}}}{C}-CH_2CH_2CN \quad (VI)$$

A mixture of 50 g of 4,4-dimethyl-5-oxohexane-nitrile, 6 g of ethylene glycol, 30 ml of petroleum ether and 0.3 g of p-toluenesulfonic acid monohydrate was reacted at the reflux temperature for 20 hours, and the reaction liquid was concentrated.

(3) Synthesis of compound of following formula (VII):

$$CH_3-\underset{\underset{\displaystyle\overset{O}{\underset{CH_2}{\diagup}}\overset{\displaystyle C-CH_3}{\underset{CH_2}{\diagdown O}}}{\overset{\displaystyle CH_3}{\displaystyle |}}}{C}-CH_2CH_2CH_2NH_2 \quad (VII)$$

A solution of 20 g of the compound of the formula (VI) in 200 ml of ether was added dropwise to 20 g of lithium aluminum hydride and 300 ml of ether over a period of 30 minutes, and reaction was carried out at the reflux temperature for 2 hours and the reaction liquid was cooled. Water was added to the reaction liquid to decompose the excess of lithium aluminum hydride. The reaction mixture was filtered, and the filtrate was concentrated.

(4) Synthesis of 2,3,3-trimethyl-3,4,5,6-tetrahydropyridine

To a solution of 20 g of the compound of the formula (VII) in 50 ml of ethanol was added 110 ml of 1N hydrochloric acid, and the mixture was heated and refluxed for 1 hour. Then, the reaction mixture was concentrated.

(5) Synthesis of 1,3,3-trimethyl-2-methylenepiperidine

A mixture of 5 g of 2,3,3-trimethyl-3,4,5,6tetrahydropyridine and 12 g of methyl tosylate was reacted at 100° C. for 4 hours. The reaction mixture was cooled and extracted with water/chloroform. Then, 2 g of sodium hydroxide was added to the water layer and the mixture was stirred. The liquid was extracted with chloroform. The chloroform layer was concentrated to obtain a yellow liquid.

(6) Synthesis of spiro-oxazine of following formula (M):

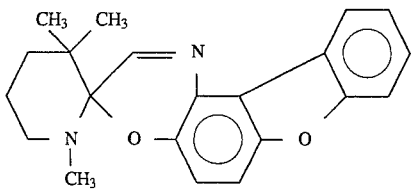

A milky white crystal of the compound of the formula (M) was prepared in the same manner as described in Example 1 except that 1,3,3-trimethyl-2-methylenepiperidine was used instead of 1,3,3-trimethyl-2-methylene-indoline.

(7) Results of Analysis

| | Elementary analysis values: | |
|---|---|---|
| | Found Value (%) | Calculated Value (%) |
| C | 75.5 | 75.5 |
| H | 6.6 | 6.6 |
| N | 8.4 | 8.4 |

EXAMPLE 21

(1) Synthesis of spiro-oxazine of following formula (N):

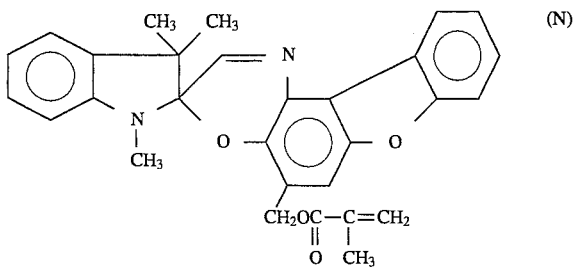

A white crystal of the spiro-oxazine of the formula (N) was prepared in the same manner as described in Example 1 except that 1-nitroso-2-hydroxy-3-methacryloxymethyldibenzofuran was used instead of 1-nitroso-2-hydroxydibenzofuran.

(2) Results of Analysis

| | Elementary analysis values: | |
|---|---|---|
| | Found Value (%) | Calculated Value (%) |
| C | 74.4 | 74.7 |
| H | 5.5 | 5.6 |
| N | 6.1 | 6.0 |

(3) Application

A glass sheet was prepared in the same manner as described in Example 7 by using the compound of the formula (N). When the glass sheet was irradiated with ultraviolet rays, the glass sheet became green, and when the light was removed and the glass sheet was allowed to stand in the dark, the glass sheet became colorless again.

EXAMPLE 22

(1) Synthesis of spiro-oxazine of following formula (O):

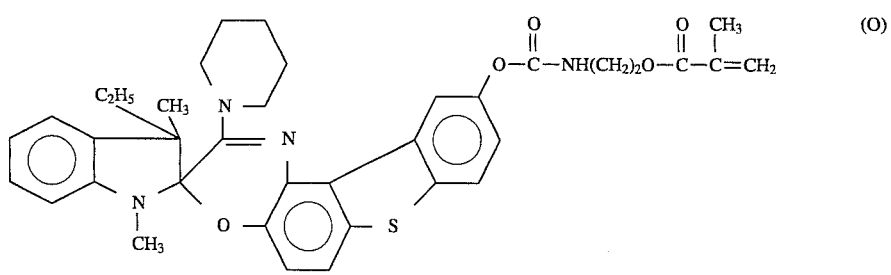

A solution comprising 15 g of 1-nitroso-2-hydroxy-8 -(N-methacryloxyethyl)carbamoyloxydibenzothiophene, 20 g of piperidine and 100 ml of trichloroethylene was heated to the reflux temperature. Then, 9 g of 1,3-dimethyl-3-ethyl-2-methylene-indoline was added dropwise to the solution being refluxed over a period of 30 minutes. After the dropwise addition, reaction was carried out at the reflux temperature for 2 hours. After the reaction, the purification was carried out in the same manner as described in Example 1 to obtain a white crystal of the spiro-oxazine of the formula (O).

(2) Results of Analysis

| | Elementary analysis values: | |
|---|---|---|
| | Found Value (%) | Calculated Value (%) |
| C | 68.1 | 68.1 |
| H | 6.2 | 6.1 |
| N | 8.5 | 8.6 |
| S | 4.6 | 4.9 |

(3) Application

When a solution of the compound of the formula (O) acetone was irradiated with ultraviolet rays, the solution became red, and when the light was removed and the solution was allowed to stand in the dark, the solution became colorless. Even when the above procedure was repeated 10 times, the photochromic characteristics were not changed at all.

EXAMPLE 23

Synthesis of spiro-oxazine of following formula (P):

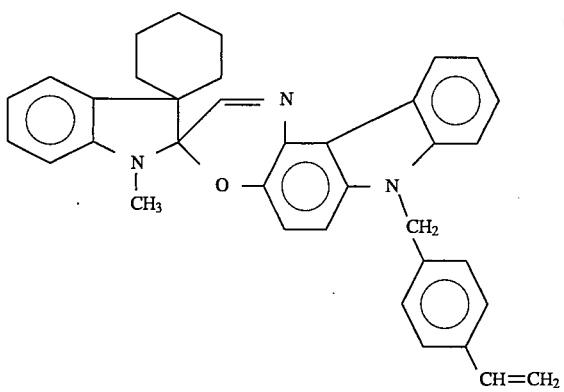

A milky white crystal of the spiro-oxazine of the formula (P) was obtained in Example 1 except that 1-methyl-3-spirocyclohexyl-2-methylene-indoline was used instead of 1,3,3-trimethyl-2-methylene-indoline and 3-hydroxy-4-nitroso-9-(4-vinyl)benzylcarbazole was used instead of 1-nitroso-2-hydroxydibenzofuran.

(2) Results of Analysis

| | Elementary analysis values: | |
|---|---|---|
| | Found Value (%) | Calculated Value (%) |
| C | 82.5 | 82.6 |
| H | 6.0 | 6.3 |
| N | 7.9 | 8.0 |

(3) Application

When a solution of the compound of Example 23 in acetone was irradiated with ultraviolet rays, the solution became red, and when the light was removed and the solution was allowed to stand in the dark, the solution became colorless again. Even when the above procedure was repeated 10 times, the photochromic characteristics were not changed at all.

EXAMPLE 24

(1) Synthesis of spiro-oxazine of following formula (Q):

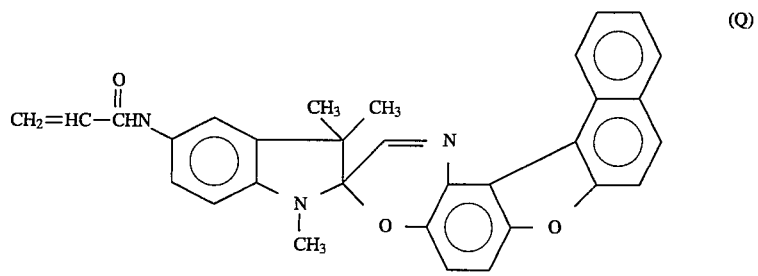

A light yellow crystal of the compound of the formula (Q) was obtained in the same manner as described in Example 1 except that 1,3,3-trimethyl-2-methylene-5-acrylaminoindoline was used instead of 1,3,3-tri-methyl-2-methylene-indoline and 8-hydroxy-9-nitroso(1,2-benzodiphenylene oxide) was used instead of 1-nitroso-2-hydroxydibenzofuran.

(2) Results of Analysis

| | Elementary analysis values: | |
|---|---|---|
| | Found Value (%) | Calculated Value (%) |
| C | 76.2 | 76.4 |
| H | 4.8 | 5.1 |
| N | 8.8 | 8.6 |

(3) Application

When a solution of the compound of the formula (Q) in acetone was irradiated with ultraviolet rays, the. solution became green, and when the light was removed and the solution was allowed to stand in the dark, the solution became colorless. Even when the above procedure was repeated 10 times, the photochromic characteristics were not changed at all.

EXAMPLE 25

(1) Synthesis of 2-hydroxy-9-methylcarbazole

To a mixture comprising 20 g of 2-hydroxycarbazole, 3 g of benzyltriethyl ammonium chloride, 70 ml of a 50% aqueous solution of sodium hydroxide and 10 ml of benzene was added dropwise 25 g of methyl iodide. After the dropwise addition, the mixture was stirred for 2 hours. The mixture was poured into hot water and the mixture was allowed to stand at room temperature overnight. The precipitated solid was recovered by filtration, washed with water and dried to obtain a yellowish brown solid of 2-hydroxy-9-methylcarbazole.

(2) Synthesis of 1-nitroso-2-hydroxy-9-methylcarbazole

A red solid of 1-nitroso-2-hydroxy-9-methylcarbazole was prepared in the same manner as described in (1) of Example 1 except that the compound obtained in (1) above was used instead of 2-hydroxydibenzofuran.

(3) Synthesis of spiro-oxazine of following formula (R):

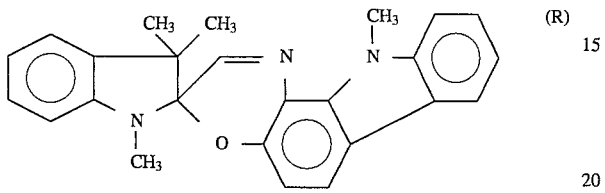

(R)

A greenish white crystal of the spiro-oxazine of the formula (R) was prepared in the same manner as described in (2) of Example 1 except that the compound obtained in (2) above was used instead of 1-nitroso-2-hydroxydibenzofuran.

(4) Results of analysis of compound of formula (R) Elementary analysis values:

| Elementary analysis values: | |
| --- | --- |
| Found Value (%) | Calculated Value (%) |
| C  78.7 | 78.7 |
| H  5.9 | 6.0 |
| N  10.8 | 11.0 |

(5) Application

When a solution of the compound of the formula (R) in acetone was irradiated with ultraviolet rays, the solution became red, and when the light was removed and the solution was allowed to stand in the dark, the solution became colorless. Even when the above procedure was repeated 10 times, the photochromic characteristics were not changed at all.

INDUSTRIAL APPLICABILITY

Since the spiro-oxazine compound of the present invention has connected benzene, heterocyclic 5-membered and benzene (or naphthalene) rings, represented by a dibenzofuran ring, the spiro-oxazine compound of the present invention has absorption peaks in both the short wavelength region (less than 550 nm) having a yellow chromophoric seed and the long wavelength region (larger than 600 nm) having a blue chromophoric seed in the visible ray region. Accordingly, a green chromophoric seed not obtainable by the conventional technique can be realized, and an abundance of hues can be selected. Therefore, the spiro-oxazine compound of the present invention is an epoch-making photochromic compound. Furthermore, the fatigue resistance is good.

Accordingly, the compound of the present invention is valuable as an optical element such as sunglasses, ski goggles or protective glass lens, or a material for currating, clothing, automobile windows, toys, writing tools, or rewritable optical disks.

We claim:

1. A spiro-oxazine compound represented by the following formula (A) or (A'):

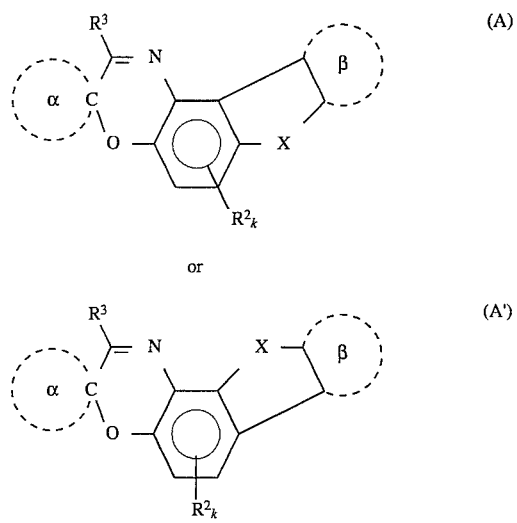

wherein, the α ring is selected from the group consisting of a 5-membered ring having one nitrogen atom and a 5-membered ring having one nitrogen atom and being connected to a benzene ring or naphthalene ring, with a proviso that the nitrogen atom in the α ring is bonded to an organic group $R^0$ and is expressed as $>N-R^0$ wherein $R^0$ is a substituent selected from the group consisting of an alkyl group having 1 to 20 carbon atoms, an alkenyl group having 2 to 20 carbon atoms, an aralkyl group having 7 to 20 carbon atoms and an aryl group having 6 to 19 carbon atoms;

the β ring is a benzene ring or a naphthalene ring;

X is selected from the group consisting of O, S, Se and $N-R^1$ wherein $R^1$ is selected from the group consisting of a hydrogen atom, an alkyl group having 1 to 20 carbon atoms, an alkenyl group having 2 to 20 carbon atoms, an aralkyl group having 7 to 20 carbon atoms, an aryl group having 6 to 19 carbon atoms and an acyl group having 2 to 20 carbon atoms;

$R^2$ and $R^3$ are each a substituent selected from the group consisting of a hydrogen atom, a hydroxyl group, an amino group having 0 to 20 carbon atoms, an alkoxy group having 1 to 20 carbon atoms, an aralkoxy group having 7 to 15 carbon atoms, an aryloxy group having 6 to 14 carbon atoms, an acyloxy group having 2 to 20 carbon atoms, an alkyl group having 1 to 20 carbon atoms, an alkenyl group having 2 to 20 carbon atoms, an aralkyl group having 7 to 15 carbon atoms, an aryl group having 6 to 14 carbon atoms, a halogen group, a cyano group, a carboxyl group, an alkoxycarbonyl group having 2 to 20 carbon atoms, a carbamoyl group having 2 to 20 carbon atoms, and a sulfonic acid group, with a proviso that $R^2$ is not a hydrogen atom; and k is an integer of from 0 to 2.

2. A spiro-oxazine compound represented by the following Formula (A) or (A'):

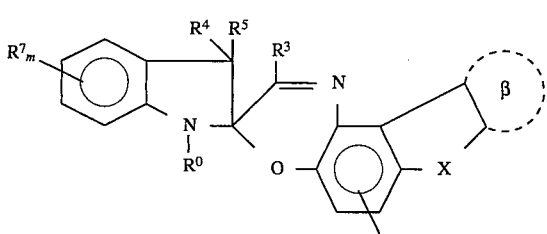

(A)

or

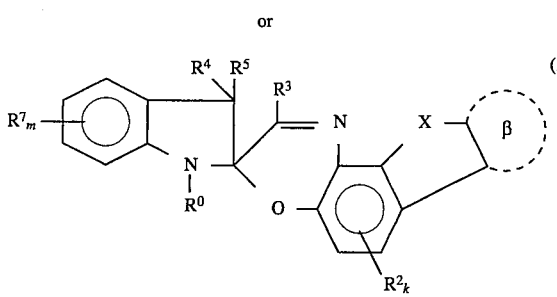

(A')

wherein,

R⁰ is a substituent selected from the group consisting of an alkyl group having 1 to 20 carbon atoms, an alkenyl group having 2 to 20 carbon atoms, an aralkyl group having 7 to 20 carbon atoms and an aryl group having 6 to 19 carbon atoms, the β ring is a benzene ring or a naphthalene ring;

X is selected from the group consisting of O, S, Se and N—$R^1$ wherein $R^1$ is selected from the group consisting of a hydrogen atom, an alkyl group having 1 to 20 carbon atoms, an alkenyl group having 2 to 20 carbon atoms, an aralkyl group having 7 to 20 carbon atoms, an aryl group having 6 to 19 carbon atoms and an acyl group having 2 to 20 carbon atoms;

$R^2$ and $R^3$ are each a substituent selected from the group consisting of a hydrogen atom, a hydroxyl group, an amino group having 0 to 20 carbon atoms, an alkoxy group having 1 to 20 carbon atoms, an aralkoxy group having 7 to 15 carbon atoms, an aryloxy group having 6 to 14 carbon atoms, an acyloxy group having 2 to 20 carbon atoms, an alkyl group having 1 to 20 carbon atoms, an alkenyl group having 2 to 20 carbon atoms, an aralkyl group having 7 to 15 carbon atoms, an aryl group having 6 to 14 carbon atoms, a halogen group, a cyano group, a carboxyl group, an alkoxycarbonyl group having 2 to 20 carbon atoms, and a sulfonic acid group, with a proviso that $R^2_k$ is not a hydrogen atom; and k is an integer of from 0 to 2.

* * * * *